United States Patent
Bauer et al.

(10) Patent No.: US 7,655,715 B2
(45) Date of Patent: *Feb. 2, 2010

(54) PHOSPHORUS-CONTAINING MIXTURES, A PROCESS FOR THEIR PREPARATION AND THEIR USE

(75) Inventors: Harald Bauer, Kerpen (DE); Mathias Dietz, Düren (DE); Ottmar Schacker, Gersthofen (DE)

(73) Assignee: Clariant Finance (BVI) Limited, Tortola (VG)

( * ) Notice: Subject to any disclaimer, the term of this patent is extended or adjusted under 35 U.S.C. 154(b) by 269 days.

This patent is subject to a terminal disclaimer.

(21) Appl. No.: 11/725,816

(22) Filed: Mar. 20, 2007

(65) Prior Publication Data

US 2007/0221893 A1 Sep. 27, 2007

(30) Foreign Application Priority Data

Mar. 21, 2006 (DE) ............ 10 2006 012 881

(51) Int. Cl.
*C08K 5/5317* (2006.01)
(52) U.S. Cl. .................... 524/133; 524/126
(58) Field of Classification Search ......... 524/462–463, 524/126, 133
See application file for complete search history.

(56) References Cited

U.S. PATENT DOCUMENTS

| | | | |
|---|---|---|---|
| 4,119,682 | A | 10/1978 | Kleiwer |
| 5,334,760 | A | 8/1994 | Wachi et al. |
| 5,710,308 | A | 1/1998 | Tawaka et al. |
| 5,750,603 | A | 5/1998 | Asrar |
| 6,855,757 | B2 | 2/2005 | Horold et al. |
| 2003/0171466 | A1 | 9/2003 | Horold et al. |

FOREIGN PATENT DOCUMENTS

| | | |
|---|---|---|
| DE | 10153780 | 11/2002 |
| EP | 1092722 | 4/2001 |
| JP | 7-179482 | 7/1995 |
| JP | 9-124668 | 5/1997 |
| JP | 1997124668 | 5/1997 |
| WO | WO 95/24445 | 9/1995 |

OTHER PUBLICATIONS

U.S. Office Action for U.S. Appl. No. 11/725,843 by Bauer et al., filed Mar. 20, 2007, mailed Jun. 23, 2008.
Co-pending U.S. Appl. No. 11/725,671, by Bauer et al., filed Mar. 20, 2007.
Co-pending U.S. Appl. No. 11/725,843, by Bauer et al., filed Mar. 20, 2007.
German Search Report for DE 102006012881.8-43, mailed Oct. 13, 2006.
European Search Report for EP 07005117, mailed May 14, 2007.
Priola et al., "Factors Influencing the Adhesion Properties of Radiation-Curable Coatings on Different Substrates," International Conference In Organic coatings Science and Technology Bd. 11, pp. 156-163 (Jul. 6, 1987).
Priola et al., "Modification of UV Curable Coatings through Addition of Functionalized Monomers." In: Special Publication—Royal Society of Chemistry (Radiation Curing of Polymers) Bd. 64. ISSN02600-6291 pp. 143-160 (1987).
English Abstract for CN 1563141, Jan. 12, 2005.

*Primary Examiner*—Peter Szekely
(74) *Attorney, Agent, or Firm*—Anthony A. Bisulca

(57) ABSTRACT

The invention relates to phosphorus-containing mixtures containing compounds of the formula $$RO-PO(A)-CH_2-CH_2-CO_2H \text{ and} \quad (I)$$

$$HO-PO(A)-CH_2-CH_2-CO_2R \quad (II)$$

in which
A is $C_1$-$C_{18}$-alkyl, $C_6$-$C_{18}$-alkylaryl, $C_6$-$C_{18}$-aralkyl or aryl,
R is $(D,E)C=C(B, R^5)$, H
B, D, E are identical or different and are each H or $C_1$-$C_{18}$-alkyl
$R^5$ is $C_1$-$C_{20}$-alkylene,
a process for their preparation and their use.

29 Claims, No Drawings

PHOSPHORUS-CONTAINING MIXTURES, A PROCESS FOR THEIR PREPARATION AND THEIR USE

The present invention is described in the German priority application No. 102006012881.8, filed Mar. 21, 2006, which is hereby incorporated by reference as is fully disclosed herein.

The invention relates to phosphorus-containing mixtures, a process for their preparation and their use.

JP-A-09/124668 describes phosphorus-containing ethylenically unsaturated monomers of the formula $$CH_2=\underset{\underset{COO(CH_2)_a O\overset{O}{\overset{\|}{C}}CHCH_2-\underset{\underset{R^3}{|}}{\overset{\overset{O}{\|}}{P}}-OR^4}}{\overset{R^1}{|}}} \quad \text{and} \quad (1)$$

$$CH_2=\underset{\underset{R^2}{|}}{\overset{R^1}{|}}CCH_2 O\overset{O}{\overset{\|}{C}}CHCH_2-\underset{\underset{R^3}{|}}{\overset{\overset{O}{\|}}{P}}-OR^4 \quad (2)$$

in which $R^1$ and $R^2$ may be hydrogen atoms and methyl groups and $R^3$ may be an alkyl, benzyl or phenyl group of 1 to 18 carbon atoms, $R^4$ may be a hydrogen atom or an alkyl group of 1 to 4 carbon atoms and m may be an integer from 2 to 4.

Copolymers which contain these monomers, in particular a phosphorus-containing ethylenically unsaturated monomer where $R^4$=H and $R^4$=Me in the molar ratios 8:2, are described here.

The abovementioned monomer is prepared by reacting phenyldichlorophosphane first with acrylic acid and methanol and then with 2-hydroxyethyl methacrylate. Since no purification step is intended, the resulting product contains considerable amounts of hydrogen-containing components. Such byproducts are undesired in high-quality plastics applications since they cause, inter alia, metal corrosion.

Halogen-containing flameproofing agents also form hydrogen halides in the event of a fire. These are corrosive and hazardous to health.

The group $R^3$ does not actively contribute toward flameproofing. It is preferably kept as small as possible. Phenyl groups are disadvantageous compared with methyl groups. They reduce the active content of phosphorus in the flameproofing agent.

This prior art teaches a person skilled in the art that monomers of the type (1) having free phosphinic acid groups or having a methyl-esterified phosphinic acid group (that cannot be introduced by reaction) are suitable for flameproofing applications.

Priola (Priola, A.; Gozzelino, G.; Ferrero, F.; Special Publication—Royal Society of Chemistry 64(1987)143-160) describes a process for the preparation of compounds of the type $$CH_2=CH-CO-O-(CH_2)_4-O-CO-(CH_2)_2-\underset{\underset{CH_3}{|}}{\overset{\overset{O}{\|}}{P}}-OH \quad (FBA1)$$

and $$CH_2=CH-CO-O-(CH_2)_4-O-\underset{\underset{CH_3}{|}}{\overset{\overset{O}{\|}}{P}}-(CH_2)_2-COOH \quad (FBA2)$$

by reacting 2-hydroxyethyl acrylate with oxaphospholane at from 10 to 20° C. to give FBA1 and at from 50 to 60° C. to give FBA2. These products are then used as adhesion promoters for UV-curable epoxyacrylate coatings on steel.

The process according to Priola envisages a reaction at from 10 to 60° C. In this temperature range, most olefinic components according to the invention are liquid and the oxaphospholane is solid. The process according to Priola has numerous disadvantages.

In the non-comminuted state, the reaction rate of the oxaphospholane is low. This is compensated by a longer reaction time. The short space-time yield which is disadvantageous in terms of process engineering is a disadvantage here, and the monomer may undergo autopolymerization owing to excessively long heat treatment and may be subject to undesired color changes. The latter can be measured by an increase in the Hazen number.

To date there has therefore been a lack of suitable phosphorus-containing compounds which also have relatively long carbon chains, can be easily prepared, can be incorporated into the polymer by reaction via double bonds (olefin) and are suitable as effective flameproofing agents.

It is therefore the object of the invention to provide a reactive halogen-free flameproofing agent which avoids the abovementioned disadvantages, can be easily prepared and has only very low halogen contents.

This object is achieved by mixtures containing compounds of the formula $$RO-P(=O)(A)\text{-}CH_2-CH_2-CO_2H \text{ and} \quad (I)$$

$$HO-P(=O)(A)\text{-}CH_2-CH_2-CO_2R \quad (II)$$

in which
A is $C_1$-$C_{18}$-alkyl, $C_6$-$C_{18}$-alkylaryl, $C_6$-$C_{18}$-aralkyl or aryl,
R is (D,E)C=C(B, $R^5$) or H
B, D, E are identical or different and are each H or $C_1$-$C_{18}$-alkyl
$R^5$ is $C_1$-$C_{20}$-alkylene.

$R^5$ is preferably a saturated, unsaturated or polyunsaturated $C_1$-$C_{20}$-alkylene.

The mixtures according to the invention preferably contain compounds of the formula $$RO-P(=O)(A)\text{-}CH_2-CH_2-CO_2H \text{ and} \quad (I)$$

$$H-OP(=O)(A)\text{-}CH_2-CH_2-CO_2-R, \text{ in which} \quad (II)$$

A is methyl, ethyl, propyl or butyl,
R is (D,E)C=C(B, $R^5$),
D being H or methyl,
E being H or methyl, B being H or methyl, $R^5$ being methylene, ethylene, n-propylene or i-propylene, tetra-, penta-, hexa-, hepta-, octa-, nona- or decamethylene.

The mixtures preferably contain from 99.9 to 20% by weight of compounds of the formula (I) and from 0.1 to 80% by weight of compounds of the formula (II), the sum of the components always being 100% by weight.

The invention also relates to a process for the preparation of mixtures according to the invention, containing compounds of the formula

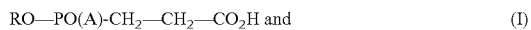  (I)

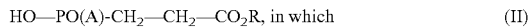  (II)

A is $C_1$-$C_{18}$-alkyl, $C_6$-$C_{18}$-alkylaryl, $C_6$-$C_{18}$-aralkyl or aryl,
R is (D,E)C=C(B, $R^5$) or H,
B, D, E are identical or different and are each H or $C_1$-$C_{18}$-alkyl
$R^5$ is $C_1$-$C_{20}$-alkylene, wherein an oxaphospholane is reacted with an olefin component.

The oxaphospholane preferably corresponds to the formula (III)

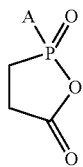

in which A is $C_1$-$C_{18}$-alkyl, $C_6$-$C_{18}$-alkylaryl, $C_6$-$C_{18}$-aralkyl or aryl.

In the process according to the invention, the mixtures preferably contain from 99.9 to 20% by weight of compounds of the formula (I) and from 0.1 to 80% by weight of compounds of the formula (II), the sum of the components always being 100% by weight.

The invention also relates to uses of mixtures as claimed in at least one of claims 1 to 4 as flame proofing agents or for the preparation of flameproofing compositions.

The invention therefore also relates to flameproofing compositions, which contain from 99.9 to 40% by weight of mixtures as claimed in at least one of claims 1 to 4 and from 0.1 to 60% by weight of olefin component, the sum of the components always being 100% by weight.

The invention also relates to a flameproofed polymer molding material, which contains from 0.5 to 50% by weight of mixtures as claimed in at least one of claims 1 to 4, from 1 to 99.5% by weight of a thermoplastic polymer or mixtures thereof, from 0 to 60% by weight of additives and from 0 to 60% by weight of filler, the sum of the components always being 100% by weight.

The thermoplastic polymers are preferably HI (high impact) polystyrene, polyphenylene ethers, polyamides, polyesters, polycarbonates and blends or polymer blends of the ABS (acrylonitrile-butadiene-styrene) or PC/ABS (polycarbonate/acrylonitrile-butadiene-styrene) type.

The invention also relates to polymer moldings, films, filaments and fibers containing from 0.5 to 50% by weight of mixtures as claimed in at least one of claims 1 to 4 or a flameproofed polymer molding material as claimed in claim 10 or 11.

The polymer of the polymer moldings, films, filaments and fibers is preferably a thermoplastic or thermosetting polymer.

The thermoplastic polymer is preferably HI (high-impact) polystyrene, polyphenylene ethers, polyamides, polyesters, polycarbonates and blends or polymer blends of the ABS (acrylonitrile-butadiene-styrene) or PC/ABS (polycarbonate/acrylonitrile-butadiene-styrene) type, polyamide, polyester and/or ABS.

The thermosetting polymers are preferably formaldehyde-, epoxy- or melamine-phenol resin polymers and/or polyurethanes.

The polymer moldings, films, filaments and fibers preferably contain from 0.5 to 50% by weight of mixtures as claimed in at least one of claims 1 to 4, from 1 to 99% by weight of polymer or mixtures thereof, from 0 to 60% by weight of additives and from 0 to 60% by weight of filler, the sum of the components always being 100% by weight.

The polymer moldings, films, filaments and fibers preferably contain from 1 to 40% by weight of mixtures as claimed in at least one of claims 1 to 4, from 1 to 99% by weight of a thermosetting polymer or mixtures thereof, from 0.5 to 60% by weight of additives and from 0.5 to 60% by weight of a filler and/or reinforcing material, the sum of the components always being 100% by weight.

The thermosetting polymer in the polymer moldings, films, filaments and fibers are preferably unsaturated polyester resins, dicyclopentadiene-modified unsaturated polyesters, polyphenylene ethers or butadiene polymers.

The polymer moldings, films, filaments and fibers are preferably used in electrical switch parts, components in automotive construction, electrical engineering, electronics, circuit boards, prepregs, potting compounds for electronic components, in boat and rotor blade construction, in outdoor GFR plastics applications, household and sanitary applications, engineering materials and further products.

A is preferably $C_1$-$C_6$-alkyl.

A is particularly preferably methyl, ethyl or propyl.

B, D and E are preferably identical or different and are each H or methyl.

$R^5$ is particularly preferably a saturated $C_1$-$C_6$-alkylene.

In particular, $R^5$ is methylene, ethylene, n-propylene, i-propylene, n-butylene or iso-butylene.

The mixtures particularly preferably contain from 99 to 30% by weight of compounds of the formula (I) and from 1 to 70% by weight of compounds of the formula (II), the sum of the components always being 100% by weight.

The mixtures according to the invention are preferably free of methyl esters.

The mixtures according to the invention preferably have a chloride content of not more than 0.005% by weight.

The mixtures according to the invention preferably contain compounds in which A is methyl, $R^5$ is $CH_2$ and D, E, B are each H:

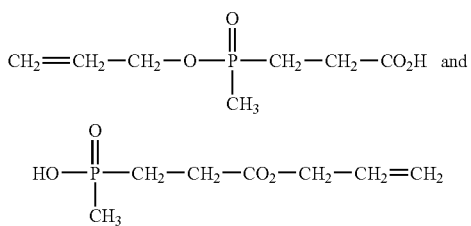

The mixtures according to the invention preferably also contain compound in which A is ethyl, $R^5$ is $CH_2$ and D, E, B are each H:

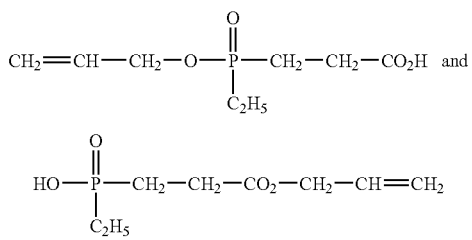

The mixtures according to the invention preferably also contain compounds in which A is phenyl, $R^5$ is $CH_2$ and D, E, B are each H:

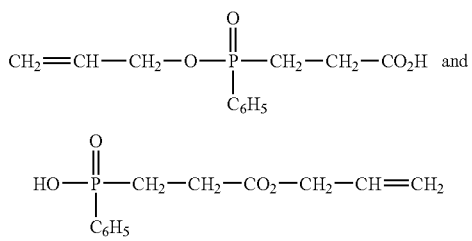

The mixtures according to the invention preferably also contain compounds in which A is methyl, $R^5$ is $CH_2$, D and E are each H and B is methyl:

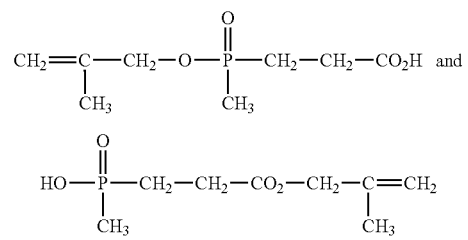

The mixtures according to the invention preferably also contain compounds in which A is ethyl, $R^5$ is $CH_2$, D and E are each H and B is methyl:

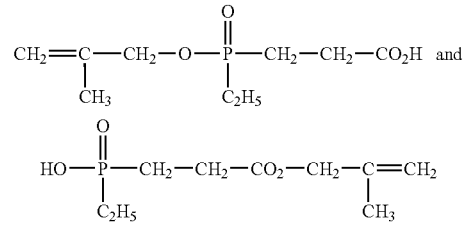

The mixtures according to the invention preferably also contain compounds in which A is phenyl, $R^5$ is $CH_2$, D and E are each H and B is methyl:

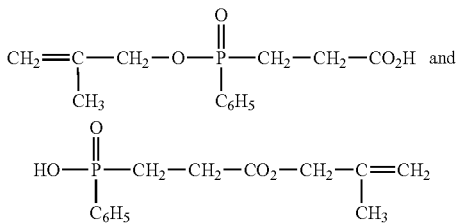

As already claimed above, A, $R^5$, D, E and B can be varied within wide limits. The present invention therefore relates not only to the mixtures described above but also to all those which are not illustrated by the representation of individual molecular schemes, including longer-chain parts in the respective compound, such as, for example, the following mixtures.

The mixtures according to the invention therefore preferably also contain compounds in which A is methyl, $R^5$ is $(CH_2)_8$, B and E are each H and D is $C_8H_{17}$:

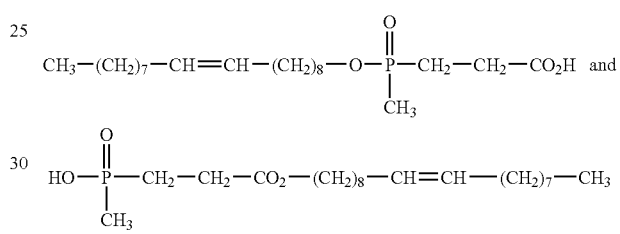

The mixtures according to the invention therefore preferably also contain compounds in which A is ethyl, $R^5$ is $(CH_2)_8$, B and E are each H and D is $C_8H_{17}$:

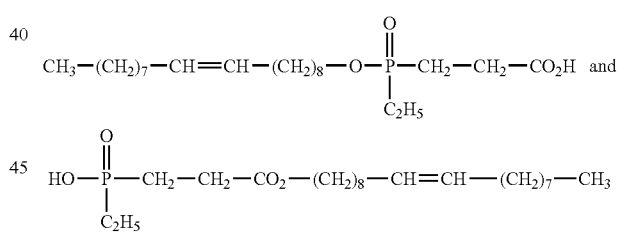

The mixtures according to the invention therefore preferably also contain compounds in which A is phenyl, $R^5$ is $(CH_2)_8$, B and E are each H and D is $C_8H_{17}$:

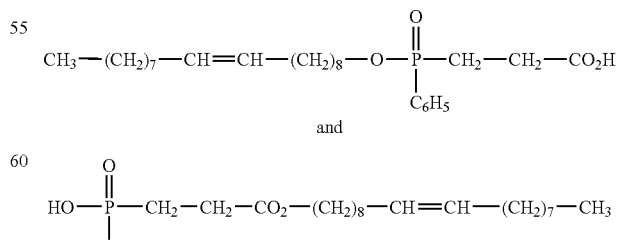

As already claimed above, A, $R^5$, D, E and B may be varied within wide limits. The present invention therefore relates not only to the mixtures described above but also to all those which are not illustrated by the representation of individual molecular schemes, including relatively long-chain moieties in the respective compound.

In principle, the mixtures according to the invention may also contain proportions of compounds of the formula RO—PO(A)-$CH_2$—$CH_2$—$CO_2R$, A and R having the meaning stated at the outset.

The mixtures according to the invention may preferably also contain from 0.1 to 80% by weight of compounds of the formula RO—PO(A)-$CH_2$—$CH_2$—$CO_2R$, A and R having the meaning stated at the outset.

In spite of only very low phosphorus contents in some cases, the mixtures according to the invention have a good flameproofing effect. They are prepared by a reaction of oxaphospholane and an olefin component. For this purpose, the olefin component can be initially introduced and oxaphospholane added or, in the opposite sequence, oxaphospholane can be initially introduced and then the olefin component added.

A is preferably $C_1$-$C_6$-alkyl.

A is particularly preferably methyl, ethyl or propyl.

The olefin component preferably corresponds to the formula (IV)

in which B, D, and E are identical or different and are each H or $C_1$-$C_{18}$-alkyl and $R^5$ is $C_1$-$C_{20}$-alkylene.

B, D and E are preferably identical or different and are each H or methyl.

$R^5$ is preferably a saturated, unsaturated or polyunsaturated $C_1$-$C_{20}$-alkylene.

$R^5$ is particularly preferably a saturated $C_1$-$C_6$-alkylene.

$R^5$ is in particular methylene, ethylene, n-propylene or i-propylene, tetra-, penta-, hexa-, hepta-, octa-, nona- or decamethylene.

In the process according to the invention, the mixtures particularly preferably contain from 99 to 30% by weight of compounds of the formula (I) and from 1 to 70% by weight of compounds of the formula (II), the sum of the components always being 100% by weight.

The oxaphospholane is preferably reacted in the form of a powder or of a melt.

The oxaphospholane is preferably 2-methyl-2,5-dioxo-1-oxa-2-phospholane, 2-ethyl-2,5-dioxo-1-oxa-2-phospholane, 2-n-butyl-2,5-dioxo-1-oxa-2-phospholane, 2-hexyl-2,5-dioxo-1-oxa-2-phospholane, 2-octyl-2,5-dioxo-1-oxa-2-phospholane or 2-phenyl-2,5-dioxo-1-oxa-2-phospholane.

The olefin component is preferably allyl alcohol, 3-buten-1-ol, 3-hydroxy-1-butene, 3-buten-2-ol, methylvinylcarbinol, 2-methyl-2-propen-1-ol, methallyl alcohol, 2-buten-1-ol, crotyl alcohol, 1-penten-3-ol, trans-2-penten-1-ol, cis-2-penten-1-ol, 3-penten-2-ol, 4-penten-1-ol, 4-penten-2-ol, 1-hexen-3-ol, cis-2-hexen-1-ol, trans-2-hexen-1-ol, cis-3-hexen-1-ol, trans-3-hexen-1-ol, 4-hexen-1-ol, 5-hexen-1-ol, 5-hexen-2-ol, 1-hepten-3-ol, 1-octen-3-ol, trans-2-octen-1-ol, oleyl alcohol or terpene alcohol.

Oxaphospholane is preferably added as a powder, and the mean particle size of the oxaphospholane is preferably from 0.1 to 1000 µm, in particular from 10 to 300 µm.

The oxaphospholane can, however, also be added as a melt. The oxaphospholane is then preferably added as a melt at a temperature of from 100 to 200° C., particularly preferably from 110 to 130° C.

The olefin component is preferably initially introduced at from 10 to 100° C. and the resulting reaction solution is likewise heated to 10 to 100° C.

The reaction is preferably effected in stirred vessels or static mixers.

Preferably used mixing units are anchor stirrers, paddle stirrers, MIG stirrers propeller stirrers, impeller stirrers, turbine stirrers, crossbeam stirrers, dispersing disks, rotor-stator mixers, static mixers, venture nozzles and/or air-lift pumps.

The reaction solution preferably experiences a mixing intensity which corresponds to a rotational Reynolds number of from 1 to 1 000 000, preferably from 100 to 100 000.

The reaction solution preferably experiences an energy input of from 0.083 to

10 $kW/m^3$, preferably 0.33-1.65 $kW/m^3$.

Preferred olefin components are unsaturated alcohols, e.g. allyl alcohol, 3-buten-1-ol, 3-hydroxy-1-butene, 3-buten-2-ol, methylvinylcarbinol, 2-methyl-2-propen-1-ol, methallyl alcohol, 2-buten-1-ol, crotyl alcohol, 1-penten-3-ol, trans-2-penten-1-ol, cis-2-penten-1-ol, 3-penten-2-ol, 4-penten-1-ol, 4-penten-2-ol, 1-hexen-3-ol, cis-2-hexen-1-ol, trans-2-hexen-1-ol, cis-3-hexen-1-ol, trans-3-hexen-1-ol, 4-hexen-1-ol, 5-hexen-1-ol, 5-hexen-2-ol, 1-hepten-3-ol, 1-octen-3-ol, trans-2-octen-1-ol, oleyl alcohol or terpene alcohol The abovementioned compounds (I) RO—P(=O)(A)-$CH_2$—$CH_2$—$CO_2H$ and (II) H—OP(=O)(A)-$CH_2$—$CH_2$—$CO_2$—R can in principle be used directly as reactive flameproofing agents. Frequently, however, the applications require physical properties which the compounds do not have. An important characteristic is the viscosity. This determines the simplicity of incorporation into the polymers.

The mixtures according to the invention exhibit the desired and required viscosity but the individual compounds (I) and (II) frequently do not, so that, in the case of the latter, auxiliaries have to be added for incorporation into the polymers.

In the flameproofing compositions according to the invention, the olefin component is used in excess amounts as auxiliaries.

The preferred viscosity of the mixtures according to the invention is from 50 to 1000 cP.

The mixtures according to the invention are preferably used as flameproofing agents. The binding of the mixtures according to the invention to the polymer preferably takes place through the reaction of the olefinic group in the respective compounds.

The flameproofing compositions preferably contain from 90 to 50% by weight of mixtures as claimed in at least one of claims 1 to 4 and from 10 to 50% by weight of olefin component, the sum of the components always being 100% by weight.

According to the invention, the phosphinic acid group or carboxyl group of the respective compound can also condense with suitable functional groups of the polymer matrix or comonomers. Preferred functional groups are hydroxyl groups.

In a process for the preparation of molding materials flameproofed according to the invention, the mixtures according to the invention a) are reacted together with other/further comonomers to give flameproofed polymers, or b) are polymerized by themselves to give a homopolymer and then blended with polymers according to the prior art by extrusion, compounding, etc., or c) are reacted with other/further comonomers to give a copolymer and then blended with polymers according to the prior art by extrusion, compounding, etc.

A process for the preparation of flameproofed polymer molding materials comprises mixing a polymer containing mixtures according to the invention with the polymer granules and possibly additives and incorporation is effected on a twin-screw extruder (ZSK 25 WLE, 14.5 kg/h, 200 rpm, L/D: 4) at temperatures of 170° C. (polystyrene), about 270° C. (PET, polyethylene terephthalate), from 230 to 260° C. (polybutylene terephthalate, PBT), 260° C. (PA6) or from 260 to 280° C. (PA 66). The homogenized polymer strand is taken off, cooled in the water bath, then granulated and dried to a residual moisture content of from 0.05 to 5%, preferably from 0.1 to 1% by weight.

The invention also relates to polymer moldings, fillers, filaments and fibers containing from 0.5 to 50% by weight of mixtures as claimed in at least one of claims 1 to 4 or a flameproofed polymer molding material which then contains the mixtures according to the invention.

The flameproofed polymer molding material preferably contains from 1 to 40% by weight of mixtures as claimed in at least one of claims 1 to 4, from 5 to 90% by weight of a thermoplastic polymer or mixtures thereof, from 5 to 40% by weight of additives and from 5 to 40% by weight of a filler, the sum of the components always being 100% by weight.

The polymer moldings, films, filaments and fibers particularly preferably contain from 1 to 40% by weight of mixtures as claimed in at least one of claims 1 to 4, from 1 to 99% by weight of a polymer or mixtures thereof, from 0 to 60% by weight of additives and from 0 to 60% by weight of a filler, the sum of the components always being 100% by weight.

Comonomers preferred according to the invention are methyl acrylate, 1,2-butadiene, 1,3-butadiene, 2-ethylhexyl acrylate, acrylamide, acrylonitrile, acrylic acid, ethyl acrylate, ethyl methacrylate, lauryl acrylate and/or methyl methacrylate, methacrylamide, methacrylonitrile, methacrylic acid, n-butyl acrylate, isobutyl acrylate, sec-butyl acrylate, n-butyl methacrylate, isobutyl methacrylate, n-hexyl acrylate, n-hexyl methacrylate, n-propyl acrylate, tert-butyl acrylate, tert-butyl methacrylate, vinyl acetate, vinyl chloride, vinylidene chloride, vinyl propionate, octyl(meth)acrylates, isooctyl(meth)acrylates, decyl (meth)acrylates, dodecyl (meth)acrylates, itaconic acid, maleic acid, cyanoalkyl(meth) acrylates, substituted acrylamides, such as N,N'-dimethylacrylamide, N-vinylpyrrolidone, N-vinylcaprolactam, N-vinylpiperidine and acrylonitrile, tricyclodecyl(meth) acrylate, isobornyl (meth)acrylates, hydroxyl(meth)acrylates, styrene, p-methylstyrene, vinyltoluene, alpha-methylstyrene.

Thermoplastic molding materials and/or moldings flameproofed according to the invention may be based on polymethyl methacrylate.

Preferred polymethyl methacrylates are homo- or copolymers of one or more of the following monomers: (meth) acrylic acid monomer having an alkyl group of 1 to 20 carbon atoms, e.g. ethyl(meth)acrylate, butyl (meth)acrylate, n-propyl(meth)acrylate, isopropyl(meth)acrylate, n-butyl (meth) acrylate, isobutyl(meth)acrylate, sec-butyl(meth)acrylate, tert-butyl(meth)acrylate, n-hexyl(meth)acrylate, cyclohexyl (meth)acrylate, n-octyl(meth)acrylate, 2-ethylhexyl(meth) acrylate, isooctyl(meth)acrylate, n-decyl(meth)acrylate, dodecyl(meth)acrylate, tricyclodecyl(meth)acrylate, hexadecyl(meth)acrylate, octadecyl (meth)acrylate, bornyl(meth) acrylate, isobornyl(meth)acrylate, menthyl (meth)acrylate, phenyl(meth)acrylate, 1-naphthyl(meth)acrylate, benzyl (meth)acrylate, 2-hydroxyethyl(meth)acrylate, cyanoalkyl (meth)acrylate, acrylamide, substituted acrylamides, e.g. N,N'-dimethylacrylamide and N-vinylpyrrolidone, N-vinylcaprolactam, N-vinylpiperidine and acrylonitrile.

Preferred uses of flameproofed thermoplastic molding materials and/or moldings according to the invention which are based on polymethyl methacrylate are automotive lighting, ships' lighting, indicator lights, traffic lights, domelights, construction glazing, illuminated advertisements, cars, optical fibers, headlamp lenses, sanitary fittings, electronic applications, monitor and display filters, parts in precision engineering, apparatus construction, measuring, drawing and writing devices, lens and spectacle glasses, optical storage media and data media, medical applications, food and medicament packagings.

The thermoplastic polymers are preferably polymers of mono- and diolefins, for example polypropylene, polyisobutylene, polybut-1-ene, poly-4-methylpent-1-ene, polyisoprene or polybutadiene, and polymers of cycloolefins, such as, for example, cyclopentene or norbornene; furthermore polyethylene (which optionally may be crosslinked), e.g. high density polyethylene (HDPE) or polyethylene having a high density and high molar mass (HDPE-HMW), polyethylene having a high density and ultra high molar mass (HDPE-UHMW), medium density polyethylene (MDPE), low density polyethylene (LDPE), linear low density polyethylene (LLDPE), branched low density polyethylene (BLDPE), and mixtures thereof.

The thermoplastic polymers are preferably copolymers of mono- and diolefins with one another or with other vinyl monomers, such as, for example, ethylene-propylene copolymers, linear low density polyethylene (LLDPE) and mixtures thereof with low density polyethylene (LDPE), propylene-1-butene copolymers, propylene-isobutylene copolymers, ethylene-1-butene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and copolymers thereof with carbon monoxide, or ethylene-acrylic acid copolymers and their salts (ionomers), and terpolymers of ethylene with propylene and a diene, such as hexadiene, cyclopentadiene or ethylidenenorbornene; furthermore mixtures of such copolymers with one another, e.g. polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ ethylene-acrylic acid copolymers and alternating or random polyalkylene/carbon monoxide copolymers and mixtures thereof with other polymers such as, for example, polyamides.

The thermoplastic polymers are preferably polyamide, polyester or ABS.

The thermoplastic polymers are preferably hydrocarbon resins (e.g. $C_5$-$C_9$), including hydrogenated modifications thereof (e.g. tackifier resins) and mixtures of polyalkylenes and starch.

The thermoplastic polymers are preferably polystyrene (polystyrene 143 E (BASF), poly(p-methylstyrene), poly-(alpha-methylstyrene).

The thermoplastic polymers are preferably copolymers of styrene or alpha-methylstyrene with dienes or acrylic derivatives, such as, for example, styrene-butadiene, styrene-acrylonitrile, styrene-alkyl methacrylate, styrene-butadiene-alkyl acrylate and methacrylate, styrene-maleic anhydride, styrene-acrylonitrile-methyl acrylate; mixtures of high impact strength obtained from styrene copolymers and another polymer, such as, for example, a polyacrylate, a diene polymer or an ethylene-propylene-diene terpolymer; and block copolymers of styrene, such as, for example, styrene-butadiene-styrene, styrene-isoprene-styrene, styrene-ethylene/butylene-styrene or styrene-ethylene/propylene-styrene.

The thermoplastic polymers are preferably graft copolymers of styrene or alpha-methylstyrene, such as, for example, styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, and mixtures thereof, as are known, for example, as so-called ABS, MBS, ASA or AES polymers.

The thermoplastic polymers are preferably halogen-containing polymers, such as, for example, polychloroprene, chlorine rubber, chlorinated and brominated copolymer of isobutylene-isoprene (halobutyl rubber), chlorinated or chlorosulfonated polyethylene, copolymers of ethylene and chlorinated ethylene, epichlorohydrin homo- and copolymers, in particular polymers of halogen-containing vinyl compounds, such as, for example, polyvinyl chloride, polyvinylidene chloride, polyvinyl fluoride, polyvinylidene fluoride; and copolymers thereof, such as vinyl chloride-vinylidene chloride, vinyl chloride-vinyl acetate or vinylidene chloride-vinyl acetate.

The thermoplastic polymers are preferably polymers which are derived from alpha-, beta-unsaturated acids and derivatives thereof, such as polyacrylates and polymethacrylates, polymethyl methacrylates impact-modified with butyl acrylate, polyacrylamides and polyacrylonitriles and copolymers of said monomers with one another or with other unsaturated monomers, such as, for example, acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

The thermoplastic polymers are preferably polymers which are derived from unsaturated alcohols and amines or acyl derivatives or acetals thereof, such as polyvinyl alcohol, polyvinyl acetate, stearate, benzoate or maleate, polyvinyl butyral, polyallyl phthalate, polyallylmelamine; and copolymers thereof with olefins.

The thermoplastic polymers are preferably homo- and copolymers of cyclic ethers, such as polyalkylene glycols, polyethylene oxide, polypropylene oxide or copolymers thereof with bisglycidyl ethers.

The thermoplastic polymers are preferably polyacetals, such as polyoxymethylene, and those polyoxymethylenes which contain comonomers, such as, for example, ethylene oxide; polyacetals which are modified with thermoplastic polyurethanes, acrylates or MBS.

The thermoplastic polymers are preferably polyphenylene oxides and sulfides and mixtures thereof with styrene polymers or polyamides.

The thermoplastic polymers are preferably polyurethanes which are derived from polyethers, polyesters and polybutadienes having terminal hydroxyl groups on the one hand and aliphatic and aromatic polyisocyanates on the other hand, and precursors thereof.

Thermoplastic polymers are polyamides and copolyamides which are derived from diamines and dicarboxylic acids and/or from aminocarboxylic acids or the corresponding lactams, such as polyamide 2/12, polyamide 4 (poly-4-aminobutyric acid, ®Nylon 4, from DuPont), polyamide 4/6 (poly(tetramethyleneadipamide), poly(tetramethyleneadipic acid diamide), ®Nylon 4/6, from DuPont), polyamide 6 (polycaprolactam, poly-6-aminohexanoic acid, ®Nylon 6, from DuPont, ®Akulon K122, from DSM; ®Zytel 7301, from DuPont; ®Durethan B 29, from Bayer), polyamide 6/6 (poly(N,N'-hexamethyleneadipamide), ®Nylon 6/6, from DuPont, ®Zytel 101, from DuPont; ®Durethan A30, ®Durethan AKV, ®Durethan AM, from Bayer; ®Ultramid A3, from BASF), polyamide 6/9 (poly(hexamethylenenonanediamide), ®Nylon 6/9, from DuPont), polyamide 6/10 (poly(hexamethylenesebacamide), ®Nylon 6/10, from DuPont), polyamide 6/12 (poly(hexamethylenedodecanediamide), ®Nylon 6/12, from DuPont), polyamide 6/66 (poly(hexamethyleneadipamide-co-caprolactam), ®Nylon 6/66, from DuPont), polyamide 7 (poly-7-aminoheptanoic acid, ®Nylon 7, from DuPont), polyamide 7,7 (polyheptamethylenepimelamide, ®Nylon 7,7, from DuPont), polyamide 8 (poly-8-aminooctanoic acid, ®Nylon 8, from DuPont), polyamide 8,8 (polyoctamethylenesuberamide, ®Nylon 8,8, from DuPont), polyamide 9 (poly-9-aminononanoic acid, Nylon 9, from DuPont), polyamide 9,9 (polynonamethyleneazelaamide, ™Nylon 9,9, from DuPont), polyamide 10 (poly-10-aminodecanoic acid, ®Nylon 10, from DuPont), polyamide 10,9 (poly(decamethyleneazelaamide), ®Nylon 10,9, from DuPont), polyamide 10,10 (polydecamethylenesebacamide, ®Nylon 10,10, from DuPont), polyamide 11 (poly-11-aminoundecanoic acid, ®Nylon 11, from DuPont), polyamide 12 (polylauryllactam, ®Nylon 12, from DuPont, ®Grillamid L20, from Ems Chemie), aromatic polyamide starting from m-xylene, diamine and adipic acid; polyamides prepared from hexamethylenediamine and iso- and/or terephthalic acid (polyhexamethyleneisophthalamide, polyhexamethyleneterephthalamide) and optionally an elastomer as a modifier, e.g. poly-2,4,4-trimethylhexamethyleneterephthalamide or poly-m-phenyleneisophthalamide; block copolymers of the abovementioned polyamides with polyolefins, olefin copolymers, ionomers or chemically bonded or grafted elastomers; or with polyethers, such as, for example, with polyethylene glycol, polypropylene glycol or polytetramethylene glycol; furthermore polyamides or copolyamides modified with EPDM or ABS; and polyamides condensed during the processing ("RIM polyamide systems").

The thermoplastic polymers are preferably polyureas, polyimides, polyamidoimides, polyetherimides, polyesterimides, polyhydantoins and polybenzimidazoles.

The polymers are preferably polyesters which are derived from dicarboxylic acids and dialcohols and/or from hydroxycarboxylic acids or the corresponding lactones, such as polyethylene terephthalate, polybutylene terephthalate (®Celanex 2500, ®Celanex 2002, from Celanese; ®Ultradur, from BASF), poly-1,4-dimethylolcyclohexane terephthalate, polyhydroxybenzoates, and block polyetheresters which are derived from polyethers having terminal hydroxyl groups; and furthermore polyesters modified with polycarbonates or MBS.

The thermoplastic polymers are preferably polycarbonates and polyestercarbonates.

The thermoplastic polymers are preferably polysulfones, polyethersulfones and polyetherketones.

A process for the preparation of flameproofed polymer moldings, wherein flameproofed polymer molding materials according to the invention are processed by injection molding (e.g. injection molding machine type Aarburg Allrounder) and pressing, foam injection molding, internal gas pressure injection molding, blow molding, foam casting, calendering, lamination and coating at relatively high temperatures to give flameproofed polymer moldings, is preferred.

A process for the preparation of flameproofed polymer moldings, wherein the flameproofed molding material according to the invention is processed at melt temperatures according to the invention to give polymer moldings.

Melt temperatures preferred according to the invention are from 200 to 250° C. in the case of polystyrene,
from 200 to 300° C. in the case of polypropylene,
from 250 to 290° C. in the case of polyethylene terephthalate (PET),
from 230 to 270° C. in the case of polybutylene terephthalate (PBT),
from 260 to 290° C. in the case of polyamide 6 (PA6),
from 260 to 290° C. in the case of polyamide 6.6 (PA 6.6),
from 280 to 320° C. in the case of polycarbonate.

The invention also relates to flameproofed thermosetting polymer moldings, films, filaments and fibers containing the mixtures according to the invention and/or the flameproofed polymer molding materials according to the invention.

The thermosetting polymer in the polymer moldings, films, filaments and fibers preferably comprises block copolymers having a polybutadiene or polyisoprene block and a block of styrene or alpha-methylstyrene.

The thermosetting polymer in the polymer moldings, films, filaments and fibers preferably comprises block copolymers having a first polybutadiene block and a second polyethylene block or ethylene-propylene block.

The thermosetting polymer in the polymer moldings, films, filaments and fibers also preferably comprises block copolymers having a first polyisoprene block and a second polyethylene block or an ethylene-propylene block.

The thermosetting polymer in the polymer moldings, films, filaments and fibers is preferably one which is based on epoxidized vegetable oils (epoxidized soybean oil/linseed oil), acrylic acid derivatives (acrylic acid, crotonic acid, isocrotonic acid, methacrylic acid, cinnamic acid, maleic acid, fumaric acid, methylmethacrylic acid) and hydroxyalkyl acrylates and/or hydroxyalkyl methacrylates (hydroxyethyl methacrylate, hydroxypropyl methacrylate, hydroxybutyl methacrylate, polyethylene glycol methacrylate).

In a process for the preparation of thermosetting molding materials, the mixtures according to the invention
a) are reacted together with other/further monomers to give flameproofed polymers, or
b) are polymerized by themselves to give a homopolymer and then blended with polymers according to prior art by extrusion, compounding, etc., or
c) are reacted with other/further monomers to give a copolymer and then crosslinked with further monomers, or
d) are grafted onto a predetermined copolymer.

The binding is preferably effected by the reaction of the olefinic group of the respective compound in the mixtures according to the invention. According to the invention, the phosphinic acid groups or carboxyl groups of the respective compounds can also be condensed with suitable functional groups of the polymer matrix. Preferred functional groups are hydroxyl groups.

The invention also relates to flame proofed thermosetting polymer molding materials, containing the mixtures according to the invention.

The thermosetting polymer preferably comprises unsaturated polyester resins (UP resins) which are derived from copolyesters of saturated and unsaturated, polybasic carboxylic acids, in particular dicarboxylic acids, or anhydrides thereof with polyhydric alcohols, and vinyl compounds as crosslinking agent.

UP resins are cured by free radical polymerization using initiators (e.g. peroxides) and accelerators.

Unsaturated polyesters may contain the ester group as a linking member in the polymer chain.

Preferred unsaturated dicarboxylic acids and dicarboxylic acid derivatives for the preparation of the polyesters are maleic acid, maleic anhydride and fumaric acid, itaconic acid, citraconic acid and mesaconic acid.

These may be mixed with up to 200 mol %, based on the unsaturated acid components, of at least one aliphatic saturated or cycloaliphatic dicarboxylic acid.

Preferred saturated dicarboxylic acids are phthalic acid, isophthalic acid, terephthalic acid, dihydrophthalic acid, tetrahydrophthalic acid, hexahydrophthalic acid, endomethylenetetrahydrophthalic acid, adipic acid, succinic acid, sebacic acid, glutaric acid, methylglutaric acid and pimelic acid.

Preferred polyhydric, in particular dihydric, optionally unsaturated alcohols are the customary alkanediols and oxaalkanediols having acyclic or cyclic groups.

Preferred dihydric alcohols are ethylene glycol, 1,2-propanediol, 1,3-propanediol, diethylene glycol, dipropylene glycol, 2,2-dimethyl-1,3-propanediol, 1,3-butanediol, 1,4-butanediol, neopentyl glycol, 1,6-hexanediol, 2,2-bis(4-hydroxycyclohexyl)propane, perhydrobisphenol and others.

Ethylene glycol, 1,2-propanediol, diethylene glycol, triethylene glycol, polyethylene glycol and dipropylene glycol, 1,2-cyclohexanediol, 2,2-bis(hydroxycyclohexyl)propane, trimethylolpropane monoallyl ether, bisphenol A, bisphenol F, dialkyl maleate, bisoxalkylated bisphenol A, ethoxylated or propoxylated bisphenol A are particularly preferred.

Monohydric, trihydric or polyhydric alcohols may be concomitantly used: methanol, ethanol, butanol, allyl alcohol, benzyl alcohol, cyclohexanol and tetrahydrofurfuryl alcohol, trimethylolpropane, ethylhexanol, fatty alcohols, benzyl alcohols, 1,2-di(allyloxy)propan-3-ol, glycerol and pentaerythritol, from mono-, di- and triallyl ethers and benzyl ethers and trihydric and polyhydric alcohols having 3-6 carbon atoms, e.g. trimethylolpropane diallyl ether, and by incorporation of monobasic acids, such as benzoic acid or acrylic acid.

Preferred unsaturated monomers copolymerizable with unsaturated polyesters preferably carry vinyl, vinylidene or allyl groups, e.g. preferably styrene, but also, for example, styrenes alkylated or alkenylated on the nucleus, it being possible for the alkyl groups to contain 1-4 carbon atoms, e.g. vinyltoluene, divinylbenzene, alpha-methylstyrene, tert-butylstyrene; vinyl esters of carboxylic acids having 2-6 carbon atoms, preferably vinyl acetate, vinyl propionate, vinyl benzoate; vinylpyridine, vinylnaphthalene, vinylcyclohexane, acrylic acid and methacrylic acid and/or their esters (preferably vinyl, allyl and methallyl esters) having 1-4 carbon atoms in the alcohol component, their amides and nitriles, maleic anhydride and maleic monoesters and diesters having 1-4 carbon atoms in the alcohol component, maleic monoamides and diamides or cyclic imides such as butyl acrylate, methyl methacrylate, acrylonitrile, N-methylmaleimide or N-cyclohexylmaleimide; allyl compounds, such as allylbenzene and allyl esters, such as allyl acetate, diallyl phthalate, diallyl isophthalate, diallyl fumarate, allyl carbonates, diallyl phthalates, diallyl carbonates, triallyl phosphate and triallyl cyanurate.

The preferred vinyl compound for crosslinking is styrene.

Preferred unsaturated polyesters may carry the ester group in the side chain too, such as, for example, polyacrylates and polymethacrylates.

Preferred curing systems are peroxides and accelerators.

Preferred accelerators are metal coinitiators and aromatic amines and/or UV light and photosensitizers, e.g. benzoin ethers.

Preferred peroxides are inorganic and/or organic peroxyacids, hydroperoxides, ozonides, di-tert-butyl peroxide, tert-butyl peroctanoate, tert-butyl perpivalate, tert-butyl per-2-ethylhexanoate, tert-butyl permaleate, tert-butyl perisobutyrate, benzoyl peroxide, diacetyl peroxide, succinyl peroxide, p-chlorobenzoyl peroxide, dicyclohexyl peroxodicarbonate, acetylacetone peroxide, methyl ethyl ketone peroxides, cyclohexane peroxides, dicumyl hydroperoxides, tert-butyl hydroperoxides, cumyl hydroperoxides, pinene hydroperoxides, terpineol ozonides.

Initiators are preferably used in amounts of from 0.1 to 20% by weight, preferably from 0.2 to 15% by weight, calculated relative to the mass of all comonomers.

Preferred metal coinitiators are cobalt, manganese, iron, vanadium, nickel or lead compounds, e.g. cobalt octanoate, cobalt(II) bis-2-ethyl hexanoate, cobalt naphthenate, vanadium acetylacetonate.

Metal coinitiators are preferably used in amounts of 0.05 to 1% by weight, calculated relative to the mass of all comonomers.

Preferred accelerators are aromatic amines, such as dimethylaniline, dimethyl-p-toluene, diethylaniline, phenyldiethanolamine, ethylamine, tert-butylamine, diethylaniline, dimethyl-p-toluidine.

Preferred accelerators are azo catalysts, such as azoisobutyronitrile, mercaptans, such as lauryl mercaptan, bis(2-ethylhexyl)sulfide and bis(2-mercaptoethyl)sulfide.

A process for the preparation of flameproofed copolymers comprises copolymerizing (A) at least one ethylenically unsaturated dicarboxylic anhydride, derived from at least one $C_4$-$C_8$-dicarboxylic acid, (B) at least one vinylaromatic compound and (C) at least one polyol, and (D) reacting the product with mixtures according to the invention.

Dicyclopentadiene-modified unsaturated polyesters which are obtained by reacting dicyclopentadiene, maleic anhydride, water, saturated alcohol and optionally a further polybasic acid can be preferably used. The polyester is crosslinked with a monomer which can be subjected to free radical polymerization, such as styrene, to give the resin.

Preferred saturated alcohols are ethylene glycol, diethylene glycol, 1,3-propanediol, 2-methyl-1,3-propanediol, 1,4-butanediol, 1,3-butanediol, 2,3-butanediol, dipropylene glycol, 1,5-pentanediol, 1,6-hexanediol, 2,2-dimethyl-1,3-propanediol, 2-ethyl-1,4-butanediol, 1,7-heptanediol, 1,8-octanediol, 1,9-nonanediol, 1,10-decanediol, 1,4-cyclohexanediol, 1,4-dimethylolcyclohexane, 2,2-diethyl-1,3-propanediol, 3-methyl-1,4-pentanediol, 2,2-diethyl-1,3-butanediol, 4,5-nonanediol, triethylene glycol, tetraethylene glycol, glycerol, trimethylolpropane, pentaerythritol, dipentaerythritol etc.

Preferred polybasic acids are maleic acid, fumaric acid, aconitic acid, itaconic acid, malonic acid, succinic acid, methylsuccinic acid, 2,2-dimethylsuccinic acid, 2,3-dimethylsuccinic acid, hexylsuccinic acid, glutaric acid, 2-methylglutaric acid, 3-methylglutaric acid, 2,2-dimethylglutaric acid, 3,3-dimethylglutaric acid, 3,3-diethylglutaric acid, adipic acid, pimelic acid, phthalic acid, isophthalic acid, terephthalic acid, etc.

The molar ratio of maleic acid to dicyclopentadiene is preferably greater than 1.5.

The polymers are preferably crosslinked polymers which are derived on the one hand from aldehydes and on the other hand from phenols, urea or melamine, such as phenol-formaldehyde, urea-formaldehyde and melamine-formaldehyde resins.

The polymers are preferably drying and non-drying alkyd resins.

The polymers are preferably crosslinkable acrylic resins which are derived from substituted acrylates, such as, for example, from epoxy acrylates, urethane acrylates or polyester acrylates.

The polymers are preferably alkyd resins, polyester resins and acrylate resins which are crosslinked with melamine resins, urea resins, isocyanates, isocyanurates, polyisocyanates or epoxy resins.

The polymers are preferably crosslinked epoxy resins which are derived from aliphatic, cycloaliphatic, heterocyclic or aromatic glycidyl compounds, e.g. products of bisphenol A diglycidyl ethers, bisphenol F diglycidyl ethers, which are crosslinked by means of customary curing agents, such as, for example, anhydrides or amines, with or without accelerators.

The polymers are preferably mixtures (polyblends) of the abovementioned polymers, such as, for example, PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PU, PC/thermoplastic PU, POM/acrylate, POM/MBS, PPO/HIPS, PPO/PA 6.6 and copolymers, PA/HDPE, PA/PP, PA/PPO, PBT/PC/ABS or PBT/PET/PC.

Preferred polyphenylene ethers are homopolymers of 2,6-dimethylphenol (2,6-dimethyl-1,4-phenylene ether), styrene graft copolymer of 2,6-dimethyl-1,4-phenylene ether, copolymer of 6-dimethylphenol and 2-methyl-6-phenylphenylene ether and the copolymer of 2,6-dimethylphenol and 2,3,6-trimethylphenol.

Preferred impact modifiers for polyphenylene ethers are comonomers, such as ethylene, propylene, 1-butene and 4-methyl-1-pentene, alkenylaromatics, such as styrene and alpha-methylstyrene, conjugated dienes, such as butadiene, and isoprene, and vinylcarboxylic acids and their derivatives, such as vinyl acetate, acrylic acid, alkylacrylic acid, ethyl acrylate, methyl methacrylate and acrylonitrile.

Preferred thermosetting plastics are polymers from the class consisting of the cyanate esters, cyanate ester/bismaleimide copolymer, bismaleimide-triazine-epoxy blends and butadiene polymers, e.g. butadiene-styrene-divinylbenzene graft terpolymers (Ricon RXBK 250 series).

Preferred butadiene polymers are block copolymers which contain 70-95% by weight of one or more monovinyl-substituted aromatic hydrocarbon compounds having 8-18 carbon atoms and 30-5% by weight of one or more conjugated dienes having 4-12 carbon atoms and optionally crosslinking agents.

Preferred monovinyl-substituted aromatic hydrocarbon compounds are styrene, 3-methylstyrene, 4-n-propylstyrene, 4-cyclohexylstyrene, 4-dodecylstyrene, 2-ethyl-4-benzylstyrene, 4-p-tolylstyrene, 4-(4-phenyl-N-butyl)styrene, 1-vinylnaphthalol and 2-vinylnaphthalol.

Preferred conjugated dienes are 1,3-butadiene, isoprene, 2,3-dimethyl-1,3-butadiene, 2,4-dimethyl-1,3-butadiene, 1,3-octadiene, 4,5-diethyl-1,3-octadiene, ethylbutadiene, piperylene, 3-butyl-1,3-octadiene and phenyl-1,3-butadiene.

Preferred crosslinking agents are divinylbenzene, 1,2,4-trivinylbenzene, 1,3-divinylnaphthalene, 1,8-divinylnaphthalene, 1,3,5-trivinylnaphthalene, 2,4-divinylbiphenyl, 3,5, 4'-trivinylbiphenyl, 1,2-divinyl-3,4-dimethylbenzene, 1,5,6-trivinyl-3,7-diethylnaphthalene, 1,3-vinyl-4,5-8-tributylnaphthalene, 2,2'-divinyl-4-ethyl-4'-propylbiphenyl.

The use of mixtures according to the invention in dielectric composite material is preferred.

Preferred dielectric composite material contains:
40-60% by weight of thermosetting polymer
60-40% by weight of inorganic particulate filler
20-60% by weight of glass reinforcing agent
0.1-20% by weight of mixtures according to the invention.

Particularly preferred dielectric composite material contains:
40-60% by weight of butadiene-styrene-divinylbenzene graft terpolymer
60-40% by weight of inorganic particulate filler
20-60% by weight of glass reinforcing agent
0.1-20% by weight of mixtures according to the invention.

The use of mixtures according to the invention in a flameproofed thermoset matrix is preferred.

The preferred flameproofed thermoset matrix contains:
25-50% by weight of resin system,
10-40% by weight of glass reinforcing agent,
5-50% by weight of filler,
0.1-20% by weight of mixtures according to the invention.

The mixtures according to the invention are preferably also used in resin systems which comprise polybutadiene or polyisoprene resins or mixtures thereof with unsaturated butadiene- or isoprene-containing polymers, which can take part in crosslinking.

A preferred polybutadiene or polyisoprene resin is ®B3000 resin (from Nippon Soda).

Preferred unsaturated butadiene- or isoprene-containing polymers are, for example, graft block copolymers having a polybutadiene or polyisoprene block with at least 50% of 1,2-addition and a thermoplastic block comprising styrene or alpha-methylstyrene, e.g. ®Kraton DX1300 (Shell Chem. Corp).

Preferred unsaturated butadiene or isoprene-containing polymers are, for example, grafted block copolymers having a first polybutadiene block and a second polyethylene block or ethylene-propylene block, e.g. ®Kraton GX1855 (Shell Chem. Corp).

Preferred unsaturated butadiene- or isoprene-containing polymers are, for example, grafted block copolymers having a first polyisoprene block and a second polyethylene block or ethylene-propylene block.

From 1 to 50% by weight, based on the total polymer content, of other cocurable copolymers can preferably be added, e.g. copolymers of butadiene or isoprene with styrene, alpha-methylstyrene, acrylate or methacrylate, acrylonitrile monomers, polymers of ethylene, ethylene-propylene copolymers and ethylene-propylene-diamine terpolymers, ethylene-ethylene oxide copolymer, natural rubber, norbornene polymers, such as polycyclopentadiene, hydrogenated styrene-isoprene-styrene copolymers and butadiene-acrylonitrile copolymers.

Additives which can preferably be used for the mixtures according to the invention are co-flameproofing agents, heat stabilizers, impact modifiers/process auxiliaries, lubricants, light stabilizers, antidripping agents, compatibilizers, fillers, reinforcing materials, nucleating agents, additives for laser marking, hydrolysis stabilizers, chain extenders, colored pigments, plasticizers and plastifying agents according to the prior art.

The process for the preparation of flame-retardant thermosetting molding materials comprises mixing a thermosetting resin with the mixtures of flameproofing composition according to the invention and pressing the resulting mixture at pressures from 3 to 10 bar and temperatures from 20 to 60° C. while wet (cold pressing).

A further process for the preparation of flame-retardant thermosetting molding materials comprises mixing a thermosetting resin with mixtures or flameproofing composition according to the invention and pressing the resulting mixture at pressures from 3 to 10 bar and temperatures from 80 to 150° C. while wet (warm or hot pressing).

Particularly preferred thermosetting plastics are also those having a natural basis, i.e. those which are based on epoxidized vegetable oils (epoxidized soybean/linseed oil), acrylic acid derivatives (acrylic acid, crotonic acid, isocrotonic acid, methacrylic acid, cinnamic acid, maleic acid, fumaric acid, methylmethacrylic acid) and hydroxyalkyl acrylates and/or hydroxyalkyl methacrylates (hydroxyethyl methacrylate, hydroxypropyl methacrylate, hydroxybutyl methacrylate, polyethylene glycol methacrylate).

Preferred uses of flameproofed thermosetting moldings are electrical switch parts, components in automotive construction, electrical engineering, electronics, circuit boards, prepregs, potting compounds for electronic components, in boat and rotor blade construction, in GFR outdoor applications, household and sanitary applications and engineering materials.

The invention is explained by the following examples. There, the following substances are used:
HEMA hydroxyethyl methacrylate
HPMA hydroxypropyl methacrylate
HBMA hydroxybutyl methacrylate
PEGMA polyethylene glycol methacrylate
HEA 2-hydroxyethyl acrylate
AAL allyl alcohol
MAL isobutenol
OAL oleyl alcohol
Oxa oxaphospholane, ®Exolit PE110

In the examples, the mixtures according to the invention are also referred to as reactive flameproofing agent according to the invention.

EXAMPLE 1

49.3 g of HEMA are initially introduced into a five-necked round-bottomed flask having a thermometer, dropping funnel, KPG stirrer and jacketed coil condenser and 50.8 g of an oxa melt at 130° C. are metered in the course of 0.1 h. The reaction solution is thermostatted at 50° C. using a thermostatting bath. A reactive flameproofing agent according to the invention, whose analytical data are listed in table 1, is obtained. The reactive flameproofing agent has a Hazen number of 25.

EXAMPLE 2 (COMPARISON)

49.3 g of HEMA and 50.8 g of an oxa powder having a mean particle diameter of 3 mm are initially introduced into a five-necked round-bottomed flask having a thermometer, dropping funnel, KPG stirrer and jacketed coil condenser. The reaction solution is thermostatted at 60° C. using a thermostatting bath. It takes 4 h before the total solid has dissolved. The reactive flameproofing agent has an (undesirably high) Hazen number of 105, which indicates substantially undesired secondary reactions.

EXAMPLE 3 (COMPARISON)

A phosphorus-containing ethylenically unsaturated monomer having the following composition is obtained according to JP 9124668: 80 mol % (corresponding to 79% by weight) of $CH_2=C(CH_3)-CO_2-CH_2CH_2O_2C-CH_2CH_2PO(OH)C_6H_5$ and 20 mol % (corresponding to 21% by weight) of $CH_2=C(CH_3)-CO_2-CH_2\quad CH_2O_2C-CH_2CH_2PO(OCH_3)C_6H_5$.

EXAMPLE 4

As in example 1, 51.8 g of HPMA are initially introduced and 48.2 g of an oxa melt at 130° C. are metered in the course of 0.04 h. The reaction solution is thermostatted at 90° C. using a thermostatting bath. A reactive flameproofing agent according to the invention, whose analytical data are listed in table 1, is obtained.

EXAMPLE 5

As in example 1, 54.1 g of HBMA are initially introduced and 45.9 g of an oxa melt at 130° C. are metered in the course of 1 h. The reaction solution is thermostatted at 30° C. using a thermostatting bath. A reactive flameproofing agent according to the invention, whose analytical data are listed in table 1, is obtained.

EXAMPLE 6

As in example 1, 72.9 g of PEGMA are initially introduced and 27.1 g of an oxa melt at 130° C. are metered in the course of 0.2 h. The reaction solution is thermostatted at 60° C. using a thermostatting bath. A reactive flameproofing agent according to the invention, whose analytical data are listed in table 1, is obtained.

EXAMPLE 7

As in example 1, 46.4 g of HEA are initially introduced and 53.6 g of an oxa melt at 130° C. are metered in the course of 0.3 h. The reaction solution is thermostatted at 60° C. using a thermostatting bath. A reactive flameproofing agent according to the invention, whose analytical data are listed in table 1, is obtained.

EXAMPLE 8

As in example 1, 30.2 g of AAL are initially introduced and 69.8 g of an oxa melt at 130° C. are metered in the course of 0.3 h. The reaction solution is thermostatted at 60° C. using a thermostatting bath. A reactive flameproofing agent according to the invention, whose analytical data are listed in table 1, is obtained.

EXAMPLE 9

As in example 1, 35 g of MAL are initially introduced and 65 g of an oxa melt at 130° C. are metered in the course of 0.1 h. The reaction solution is thermostatted at 50° C. using a thermostatting bath. A reactive flameproofing agent according to the invention, whose analytical data are listed in table 1, is obtained.

EXAMPLE 10

As in example 1, 66.7 g of MAL are initially introduced and 33 g of an oxa melt at 130° C. are metered in the course of 0.1 h. The reaction solution is thermostatted at 60° C. using a thermostatting bath. A reactive flameproofing agent according to the invention, whose analytical data are listed in table 1, is obtained.

EXAMPLE 11

51.6 g of HEMA are initially introduced into a five-necked round-bottomed flask having a thermometer, dropping funnel, KPG stirrer and jacketed coil condenser and 48.4 g of an oxa melt at 130° C. are metered in the course of 0.1 h. The reaction solution is thermostatted at 50° C. using a thermostatting bath. A flameproofing composition according to the invention, whose analytical data are listed in table 2, is obtained.

EXAMPLE 12

74.4 g of HEMA are initially introduced into a five-necked round-bottomed flask having a thermometer, dropping funnel, KPG stirrer and jacketed coil condenser and 25.6 g of an oxa melt at 130° C. are metered in the course of 0.1 h. The reaction solution is thermostatted at 50° C. using a thermostatting bath. A flameproofing composition according to the invention, whose analytical data are listed in table 2, is obtained.

EXAMPLE 13

56.4 g of HPMA are initially introduced into a five-necked round-bottomed flask having a thermometer, dropping funnel, KPG stirrer and jacketed coil condenser and 25.6 g of an oxa melt at 130° C. are metered in the course of 0.04 h. The reaction solution is thermostatted at 90° C. using a thermostatting bath. A flameproofing composition according to the invention, whose analytical data are listed in table 2, is obtained.

EXAMPLE 14

49.5 g of MAL are initially introduced into a five-necked round-bottomed flask having a thermometer, dropping funnel, KPG stirrer and jacketed coil condenser and 50.6 g of an oxa melt at 130° C. are metered in the course of 0.1 h. The reaction solution is thermostatted at 50° C. using a thermostatting bath. A flameproofing composition according to the invention, whose analytical data are listed in table 2, is obtained.

EXAMPLE 15

13.3 g of reactive flameproofing agent of example 1 were initially introduced, and a further 120 g of methyl methacrylate and 60 mg of 2,2'-azobisisobutyronitrile (AIBN) were added. Stirring was then effected for 10 min at room temperature. The mixture is introduced between two glass plates and polymerized at 60° C. for 48 h. Thereafter, the glass plates are thoroughly polymerized for 3 h at 100° C. in a drying oven to almost 100% conversion. The glass plates are removed and the transparent sheet (thickness 3.2 mm) is cut into 12.7 mm wide and 10 cm long strips. These test specimens have the flameproofing agent content listed in table 3 and achieve the LOI listed in table 3.

EXAMPLE 16 (COMPARISON)

As in example 15, a test specimen was produced using the reactive flameproofing agent from example 3, and the LOI of said test specimen was determined. Flameproofing agent content and LOI are listed in table 3.

EXAMPLE 17

An unsaturated polyester resin was prepared by subjecting 415 parts by weight of maleic anhydride, 419 parts by weight of phthalic anhydride, 774 parts by weight of neopentyl glycol and 159 parts by weight of n-tetradecanol to polycondensation. Furthermore, 654 parts of the reactive flameproofing agent from example 4 are added. Sixty parts by weight of the polyester were dissolved in 40 parts by weight of vinyl versatate-10. 0.25 ml of a solution of cobalt octanoate in dioctyl phthalate (1% by weight of Co) and 1 ml of a 50% strength solution of methyl ethyl ketone peroxide in dimethyl phthalate are added to 25 g of the resin. Sheets having a layer thickness of 3 mm were cast and test specimens were cut to size. The flameproofing agent content and the LOI achieved are listed in table 3.

EXAMPLE 18 (COMPARISON)

As in example 17, test specimens are produced using the reactive flameproofing agent from example 3. The flameproofing agent content and the LOI achieved are listed in table 3.

EXAMPLE 19

100 parts by weight of preaccelerated dicyclopentadienyl resin (Norpol 507-504), 37 parts by weight of reactive flameproofing agent from example 9, 2 parts by weight of peroxide curing agent (Butanox M 50), 0.5 part by weight of accelerator (cobalt-(II) bis(2-ethylhexanoate), NL 49P) are homogenized and sheets having a thickness of 3 mm are cast and are cut to give test specimens. The flameproofing agent content and the LOI achieved are listed in table 3.

EXAMPLE 20 (COMPARISON)

As in example 19, test specimens are produced using the reactive flameproofing agent from example 3. The flameproofing agent content and the LOI achieved are listed in table 3.

EXAMPLE 21

60 parts by weight of a polyester resin solution, which was prepared from maleic anhydride and 1,2-propylene glycol in the molar ratio 1:1 and dissolved in styrene to give a 65% strength solution and stabilized with 120 ppm of hydroquinone, and 40 parts by weight of a 36% strength solution of polymethyl methacrylate in styrene, which solution was stabilized with 100 ppm of hydroquinone and 1200 ppm of 2,6-dimethylquinone, were used with 3 parts by weight of magnesium hydroxide, 3 parts of tert-butyl perbenzoate (50% strength in dioctyl phthalate), 2 parts by weight of a solution of cobalt octanoate in dioctyl phthalate (1% by weight of Co), 150 parts by weight of chalk, 4.5 parts by weight of zinc stearate and 32.9 parts by weight of reactive flameproofing agent from example 7.

96 parts of a glass fiber mat comprising cut rovings about 2.6 cm long were impregnated with this resin solution and stored between polyethylene films for 14 days at 23° C. for thickening. After removal of the cover films, the thickened molding materials were pressed in a polished steel mold for 3 min at 145° C. at a pressure of 7.45 N/mm². Test specimens were cut to size. The flameproofing agent content and the LOI achieved are listed in table 3.

EXAMPLE 22 (COMPARISON)

As in example 21, test specimens are produced using the reactive flameproofing agent from example 3. The flameproofing agent content and the LOI achieved are listed in table 3.

EXAMPLE 23

A resin was prepared from 60 parts by weight of arylated polyphenylene ether, 46 parts by weight of triallyl isocyanurate, 25 parts by weight of reactive flameproofing agent from example 1, 15 parts by weight of HU-119 (silicone, Dow Corning Toray Silicone, Inc.), and 4 parts by weight of accelerator, which was dissolved in toluene (®Par butyl P, Nippon Oil & Fats Co., Ltd.). A 100 μm thick prepreg having a 50% proportion of resin was produced from the resin by immersing glass fabric. Eight of these prepregs were stacked one on top of the other. A 35 μm thick copper foil was added on the bottom and top, and this stack was hot-pressed for 100 min at 4 MPa pressure and 170° C. A 1 mm thick laminate was obtained. Test specimens are cut to size. The flameproofing agent content, the Tg achieved and the UL-94 classification achieved are listed in table 3.

EXAMPLE 24

As in example 23, test specimens are produced using the reactive flameproofing agent from example 3. The flameproofing agent content, the Tg achieved and the UL-94 classification achieved are listed in table 3.

EXAMPLE 25

1 kg of Ricon XBK 250 styrene-butadiene-divinylbenzene terpolymer (Ricon Resins, Inc., Grand Junction, Colo.) are dissolved in 1 kg of toluene, and impurities are filtered off through a 300 μm sieve. A solution of 45 g of dicumyl peroxide, dissolved in 100 g of toluene, is metered in into the solution. 1 kg of synthetic magnesium aluminum silicate (INCOR Corporation, HC-II, 400 μm) and 1150 g of reactive flameproofing agent according to the invention from example 4 are slowly admixed. In addition, 600 g of toluene are added in order to facilitate the homogenization of the mixture. The solids content of the solution is 50-60%. The mixture is filtered once again through a 50 μm sieve. An E-glass fabric is coated with the solution so that the following composition results: 20% by weight of glass fabric, 40% of polymer and 40% filler. The coated fabric is cured at 300° C. Six layers and a copper foil layer are pressed to give a laminate. Test specimens are cut to size. The flameproofing agent content and the UL-94 classification achieved are listed in table 3.

EXAMPLE 26

As in example 25, test specimens are produced using the reactive flameproofing agent from example 3. The flameproofing agent content and the UL-94 classification achieved are listed in table 3.

EXAMPLE 27

14.6 parts by weight of B3000 resin (Nippon Soda), 3.8 parts by weight of Kraton rubber (Shell Chemicals), 0.6 part by weight of Luperox 500R (Elf Atochem), 51 parts by weight of Aerosil 200 pyrogenic silica (Degussa), which was coated with 0.5 part by weight of A176 silane (OSi), and 7.4 parts by weight of reactive flameproofing agent according to example 8 are homogeneously mixed to give a slurry. Glass fabric is impregnated with the slurry and a prepreg is thus formed. 5 prepregs are pressed with one or two layers of copper foil at 165-218° C. to give a sheet. Test specimens are cut to size. The flameproofing agent content and the UL-94 classification achieved are listed in table 3.

EXAMPLE 28

As in example 27, test specimens are produced using the reactive flameproofing agent from example 3. The flameproofing agent content and the UL-94 classification achieved are listed in table 3.

TABLE 1

Flameproofing agents

| | Starting materials | | | | Analysis of flameproofing agent | | | | | |
| --- | --- | --- | --- | --- | --- | --- | --- | --- | --- | --- |
| | | Olefin component (OC) | | OC/ Oxa [mol/ | P content % by | Content of (I) % by | Content of (II) % by | Content of (III) % by | Content of OC % by | Chloride content |
| Example | Oxa [g] | Type | [g] | mol] | weight | weight | weight | weight | weight | [%] |
| 1 | 50.8 | HEMA | 49.3 | 1 | 11.7 | 99.0 | 1.0 | 0 | 0.0 | 0.0008 |
| 3 | — | — | — | — | 9.4 | 0 | 79 | 21 | 0.0 | |
| 4 | 48.2 | HPMA | 51.8 | 1 | 11.1 | 98.9 | 1.1 | 0 | 0.0 | 0.0008 |
| 5 | 45.9 | HBMA | 54.1 | 1 | 10.6 | 96.6 | 3.4 | 0 | 0.0 | 0.0007 |
| 6 | 27.1 | PEGMA | 72.9 | 1 | 6.3 | 95.7 | 4.3 | 0 | 0.0 | 0.0004 |
| 7 | 53.6 | HEA | 46.4 | 1 | 12.4 | 92.1 | 7.9 | 0 | 0.0 | 0.0009 |
| 8 | 69.8 | AAL | 30.2 | 1 | 16.1 | 97.4 | 2.6 | 0 | 0.0 | 0.0011 |
| 9 | 65.0 | MAL | 35.0 | 1 | 15.0 | 82.1 | 17.9 | 0 | 0.0 | 0.0010 |
| 10 | 33.3 | OAL | 66.7 | 1 | 7.7 | 98.3 | 1.7 | 0 | 0.0 | 0.0005 |

TABLE 2

Flameproofing compositions

| | Starting materials | | | | Analysis of flameproofing composition | | | | | | |
| --- | --- | --- | --- | --- | --- | --- | --- | --- | --- | --- | --- |
| | | Olefin component (OC) | | OC/ Oxa [mol/ | P content % by | Content of (I) % by | Content of (II) % by | Content of (III) % by | Content of OC % by | Chloride content | Viscosity |
| Example | Oxa [g] | Type | [g] | mol] | weight | weight | weight | weight | weight | [%] | [cP] |
| 1 | | | | | | | | | | | 6950 |
| 11 | 48.4 | HEMA | 51.6 | 1.1 | 11.2 | 94.4 | 0.9 | 0 | 4.6 | 0.0008 | 700 |
| 12 | 25.6 | HEMA | 74.4 | 3 | 5.9 | 49.9 | 0.5 | 0 | 49.6 | 0.0004 | 150 |
| 4 | | | | | | | | | | | 16950 |
| 13 | 43.7 | HPMA | 56.4 | 1.2 | 10.1 | 89.6 | 1.0 | 0 | 9.4 | 0.0008 | 950 |
| 14 | 49.5 | MAL | 50.6 | 1.9 | 11.4 | 62.4 | 13.6 | 0 | 23.9 | 0.0007 | 100 |

I: R—P(CH3;Ph)(O)CH2CH2CO2H via 31P-NMR
II: HO—P(CH3;Ph)(O)CH2CH2CO2R via 31 P-NMR
III: H3C—O—P(CH3;Ph)(O)CH2CH2CO2R

TABLE 3

Data on flameproofed polymer moldings

| Example | FPA from Example | FPA content [%] | P content [%] | LOI [% O2] | Tg [°C.] | Loss factor | UL-94 classification |
|---|---|---|---|---|---|---|---|
| 15 | 1 | 10 | 1.2 | 31 | — | — | — |
| 16 | 3 | 10 | 0.9 | 27.0 | — | — | — |
| 17 | 4 | 26.9 | 3 | 30 | — | — | — |
| 18 | 3 | 26.9 | 2.5 | 28 | — | — | — |
| 19 | 9 | 27.0 | 4.1 | 30 | — | — | — |
| 20 | 3 | 27.0 | 2.5 | 25 | — | — | — |
| 21 | 7 | 24.2 | 3.0 | 27 | — | — | — |
| 22 | 3 | 24.2 | 2.3 | 23 | — | — | — |
| 23 | 1 | 16.7 | 2.0 | — | 180 | 0.0025 | V-0 |
| 24 | 3 | 20.8 | 2.0 | — | 160 | 0.0035 | V-0 |
| 25 | 4 | 36 | 4.0 | — | — | 0.002 | V-0 |
| 26 | 3 | 42.6 | 4.0 | — | — | 0.004 | V-0 |
| 27 | 8 | 9.4 | 1.5 | — | — | 0.002 | V-0 |
| 28 | 3 | 6.5 | 1.5 | — | — | 0.0035 | V-0 |

Loss factor measured at 1 GHz
UL-94 classification: according to method of Underwriter Laboratories
LOI Limiting Oxygen Index
Tg glass transition temperature
FPA: flameproofing agent

The invention claimed is:

1. A mixture comprising compounds of the formulas

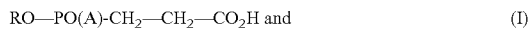

RO—PO(A)-CH$_2$—CH$_2$—CO$_2$H and  (I)

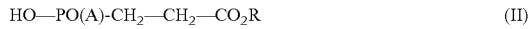

HO—PO(A)-CH$_2$—CH$_2$—CO$_2$R  (II)

wherein
A is methyl, ethyl, propyl or butyl,
R is (D,E)C═C(B, R$^5$)
B, D, E are identical or different and are each H or methyl
R$^5$ is a saturated or unsaturated or polyunsaturated C$_1$-C$_{20}$-alkylene.

2. The mixture as claimed in claim 1, comprising compounds of the formula

RO—P(═O)(A)-CH$_2$—CH$_2$—CO$_2$H and  (I)

H—OP(═O)(A)-CH$_2$—CH$_2$—CO$_2$—R, wherein  (II)

A is methyl, ethyl, propyl or butyl,
R is (D,E)C═C(B, R$^5$),
D being H or methyl,
E being H or methyl,
B being H or methyl,
R$^5$ is a saturated or unsaturated or polyunsaturated C$_1$-C$_{20}$-alkylene.

3. The mixture as claimed in claim 1, comprising from 99.9 to 20% by weight of the compound of the formula (I) and from 0.1 to 80% by weight of the compound of the formula (II), the sum of the components always being 100% by weight.

4. A process for the preparation of mixtures comprising compounds of the formula

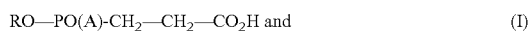

RO—PO(A)-CH$_2$—CH$_2$—CO$_2$H and  (I)

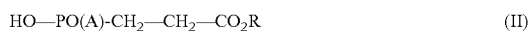

HO—PO(A)-CH$_2$—CH$_2$—CO$_2$R  (II)

wherein
A is methyl, ethyl, propyl or butyl,
R is (D,E)C═C(B, R$^5$),
B, D, E are identical or different and are each H or methyl
R$^5$ is a saturated, unsaturated or polyunsaturated C$_1$-C$_{20}$-alkylene, comprising the step of reacting an oxaphospholane with an olefin component.

5. The process as claimed in claim 4, wherein the oxaphospholane is of the formula (III)

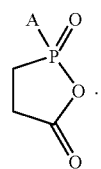

6. The process as claimed in claim 4, wherein the mixtures comprises from 99.9 to 20% by weight of the compound of the formula (I) and from 0.1 to 80% by weight of the compound of the formula (II), the sum of the components always being 100% by weight.

7. A process for the preparation of a flameproofing composition comprising the step of adding a mixture as claimed in claim 1 to the flameproofing composition during production of the flameproofing composition.

8. A flameproofing composition, comprising from 99.9 to 40% by weight of a mixture as claimed in claim 1 and from 0.1 to 60% by weight of olefin component, the sum of the components always being 100% by weight.

9. A flameproofed polymer molding material, comprising from 0.5 to 50% by weight of a mixture as claimed in claim 1, from 1 to 99% by weight of a thermoplastic polymer or a mixture thereof, from 0 to 60% by weight of additives and from 0 to 60% by weight of a filler, the sum of the components always being 100% by weight.

10. The flameproofed polymer molding material as claimed in claim 9, wherein the thermoplastic or mixture thereof are high-impact polystyrene, polyphenylene ether, polyamides, polyesters, and polycarbonates blends or polymer blends of acrylonitrile-butadiene-styrene polycarbonate/acrylonitrile-butadiene-styrene.

11. A polymer molding, film, filament or fiber comprising at least one polymer and from 0.5 to 50% by weight of a mixture as claimed in claim 1.

12. The polymer molding, film, filament or fiber as claimed in claim 11, wherein the at least one polymer is a thermoplastic or thermosetting polymer.

13. The polymer molding, film, filament or fiber as claimed in claim 11, wherein the at least one polymer is a thermoplastic polymer and wherein the thermoplastic polymer is high-impact polystyrene, polyphenylene ether, polyamides, polyesters, polycarbonates blends or polymer blends of acrylonitrile-butadiene-styrene polycarbonate/acrylonitrile-butadiene-styrene, polyamide, polyester acrylonitrile-butadiene-styrene or mixtures thereof.

14. The polymer molding, film, filament or fiber as claimed in claim 11, wherein the at least one polymer is a thermosetting polymer and wherein the thermosetting polymer is formaldehyde-, epoxy- or melamine-phenol resin polymers polyurethanes or mixtures thereof.

15. The polymer molding, film, filament or fiber as claimed in claim 11, comprising from 0.5 to 50% by weight of the mixture, from 1 to 99% by weight of a the at least one polymer, from 0 to 60% by weight of additives and from 0 to 60% by weight of a filler, the sum of the components always being 100% by weight.

16. The polymer molding, film, filament or fiber as claimed in claim 11, comprising from 1 to 40% by weight of the mixture, from 1 to 99% by weight of the at least one polymer, wherein the at least one polymer is a thermosetting polymer or a mixture thereof, from 0.5 to 60% by weight of additives and from 0.5 to 60% by weight of a filler, reinforcing material or both, the sum of the components always being 100% by weight.

17. The polymer molding, film, filament or fiber as claimed in claim 16, wherein the thermosetting polymer or mixture thereof is selected from the group consisting of unsaturated polyester resins, dicyclopentadiene-modified unsaturated polyesters, polyphenylene ethers and butadiene polymers.

18. An article comprising a polymer molding, film, filament or fiber as claimed in claim 16, wherein the article is selected from the group consisting of electrical switch parts, components in automotive construction, electrical engineering, electronics, circuit boards, prepregs, potting compounds for electronic components, boat and rotor blade construction, in GFR outdoor applications, household and sanitary applications and engineering materials.

19. A mixture of compounds made in accordance with the process as claimed in claim 4.

20. A flameproofing agent comprising a mixture as claimed in claim 1.

21. A flameproofing composition made in accordance with the process as claimed in claim 7.

22. A polymer molding, film, filament or fiber comprising at least one polymer and from 0.5 to 50% by weight of a flameproofed polymer molding material as claimed in claim 9.

23. The polymer molding, film, filament or fiber as claimed in claim 22, wherein the at least one polymer is a thermoplastic or thermosetting polymer.

24. The polymer molding, film, filament or fiber as claimed in claim 22, wherein the at least one polymer is a thermoplastic polymer and wherein the thermoplastic polymer is high-impact polystyrene, polyphenylene ether, polyamides, polyesters, polycarbonates blends or polymer blends of acrylonitrile-butadiene-styrene polycarbonate/acrylonitrile-butadiene-styrene, polyamide, polyester acrylonitrile-butadiene-styrene or mixtures thereof.

25. The polymer molding, film, filament or fiber as claimed in claim 22, wherein the at least one polymer is a thermosetting polymer and wherein the thermosetting polymer is formaldehyde-, epoxy- or melamine-phenol resin polymers polyurethanes or mixtures thereof.

26. The polymer molding, film, filament or fiber as claimed in claim 22, comprising from 0.5 to 50% by weight of the mixture, from 1 to 99% by weight of a the at least one polymer, from 0 to 60% by weight of additives and from 0 to 60% by weight of a filler, the sum of the components always being 100% by weight.

27. The polymer molding, film, filament or fiber as claimed in claim 22, comprising from 1 to 40% by weight of the mixture, from 1 to 99% by weight of the at least one polymer, wherein the at least one polymer is a thermosetting polymer or a mixture thereof, from 0.5 to 60% by weight of additives and from 0.5 to 60% by weight of a filler, reinforcing material or both, the sum of the components always being 100% by weight.

28. The polymer molding, film, filament or fiber as claimed in claim 27, wherein the thermosetting polymer or mixture thereof is selected from the group consisting of unsaturated polyester resins, dicyclopentadiene-modified unsaturated polyesters, polyphenylene ethers and butadiene polymers.

29. An article comprising a polymer molding, film, filament or fiber as claimed in claim 27, wherein the article is selected from the group consisting of electrical switch parts, components in automotive construction, electrical engineering, electronics, circuit boards, prepregs, potting compounds for electronic components, boat and rotor blade construction, in GFR outdoor applications, household and sanitary applications and engineering materials.

* * * * *